(12) United States Patent
Fetzer et al.

(10) Patent No.: US 8,899,113 B2
(45) Date of Patent: Dec. 2, 2014

(54) APPARATUS AND METHOD FOR INSPECTING A TUBE

(75) Inventors: Barry A. Fetzer, Renton, WA (US); Navpreet S. Grewal, Redmond, WA (US); Peter Kuk-kyung Hwang, Kent, WA (US); William R. Schell, Edgewood, WA (US); Kate Brown Boudreau, Seattle, WA (US)

(73) Assignee: The Boeing Company, Chicago, IL (US)

( * ) Notice: Subject to any disclaimer, the term of this patent is extended or adjusted under 35 U.S.C. 154(b) by 234 days.

(21) Appl. No.: 13/482,409

(22) Filed: May 29, 2012

(65) Prior Publication Data

US 2013/0319120 A1 Dec. 5, 2013

(51) Int. Cl.
*G01N 29/04* (2006.01)

(52) U.S. Cl.
USPC ............................................. 73/623; 73/628

(58) Field of Classification Search
USPC .......................................... 73/623, 628, 588
See application file for complete search history.

(56) References Cited

U.S. PATENT DOCUMENTS

| | | | |
|---|---|---|---|
| 4,991,427 A * | 2/1991 | Nottingham et al. | 73/623 |
| 5,485,084 A * | 1/1996 | Duncan et al. | 324/225 |
| 6,886,407 B1 | 5/2005 | Fredenberg | |
| 7,415,882 B2 * | 8/2008 | Fetzer et al. | 73/634 |
| 7,464,596 B2 | 12/2008 | Bui | |
| 7,562,576 B2 | 7/2009 | Fetzer | |
| 7,637,163 B2 | 12/2009 | Fetzer | |
| 7,644,618 B2 | 1/2010 | Fetzer | |
| 7,690,259 B2 * | 4/2010 | Bui et al. | 73/625 |
| 7,975,549 B2 | 7/2011 | Fetzer | |
| 2003/0136195 A1 * | 7/2003 | Krieg et al. | 73/628 |
| 2003/0188589 A1 * | 10/2003 | Harthorn et al. | 73/865.8 |
| 2007/0152054 A1 * | 7/2007 | Bonavides et al. | 235/454 |
| 2009/0078742 A1 * | 3/2009 | Pasquali et al. | 228/103 |
| 2010/0313664 A1 * | 12/2010 | Cain, Jr. | 73/623 |

OTHER PUBLICATIONS

European Search Report for Application No. EP13167923.5 issued on Sep. 9, 2013.
Tube-Mac Industries, "Pyplok Installation Guide," retrieved on May 16, 2012.

\* cited by examiner

*Primary Examiner* — Hezron E Williams
*Assistant Examiner* — Xin Zhong (57) ABSTRACT

An apparatus for inspecting a tubular workpiece may include a probe assembly and a rotation mechanism. The probe assembly may include a transducer array positionable adjacent to an inner surface of the tubular workpiece. The probe assembly may generate transmitted sound waves and may receive reflected sound waves. The rotation mechanism may rotate the probe assembly relative to the tubular workpiece in a manner such that the transducer array passes over the inner surface in a circumferential direction during transmission of the transmitted sound waves.

8 Claims, 10 Drawing Sheets

APPARATUS AND METHOD FOR INSPECTING A TUBE

FIELD

The present disclosure relates generally to non-destructive inspection of structures and, more particularly, to ultrasonic inspection of structures.

BACKGROUND

Structures are commonly inspected after fabrication to assess the quality of the structure prior to placing the structure into service. During inspection, a structure may be examined to locate and identify anomalies. For example, a structure may be inspected to locate potential flaws that may exist in the material that makes up the structure. Inspection of a structure may also include measuring the size, shape, and orientation of one or more features of the structure to determine whether such features fall within design tolerances. Measurement of certain features may provide an indication of the integrity of the structure or the integrity of a joint between two components that make up the structure.

For example, metallic tubing for carrying fluids is typically inspected to check the quality of the joint between the tube and a fitting that may be mounted on an end of the tube. A fitting may be mechanically joined to a tube end using a swaging process to form a swage joint wherein the walls of the tube end may be outwardly expanded and forced into grooves in the interior circumference of the fitting to effectively interlock the fitting and the tube. The integrity of the swage joint may be assessed by measuring the increase in the inner diameter of the tube end relative to the nominal diameter of the tube in a non-expanded location. If the increased diameter of the tube end is within a predetermined dimensional range, then the swage joint may pass inspection.

Conventional methods for inspecting swage joints include mechanical measurement techniques. One measurement technique includes the use of a bore gauge having opposing telescopic portions. The bore gauge may be inserted into the end of a tube at the location where a fitting is swaged onto the tube. The telescopic portions of the bore gauge may be outwardly extended until the tips of the telescopic portions contact opposite sides of the inner surface of the tube end. The telescopic portions may then be locked into position and the bore gauge may be removed from the tube. The distance across the tips of the telescopic portions may be measured using a second mechanical device such as a caliper to determine the inner diameter of the tube end for comparison to a predetermined dimensional range.

Unfortunately, the accuracy with which the inner diameter of a tube end may be measured using a bore gauge may depend to a large extent on the skill of the technician. For example, accurate measurement of the inner diameter of a tube at a swage joint may depend upon the skill of the technician in accurately positioning the bore gauge such that each one of the opposing telescoping portions contacts the inner surface of the tube at diametrically opposed locations. As may be appreciated, accurate measurement of the inner diameter of a swage joint using a mechanical measurement technique may present repeatability issues from technician to technician.

In addition, mechanical measurement techniques may present challenges in measuring the inner diameter of a swage joint with the required degree of precision on a repeatable basis. For example, in certain applications, assessing the integrity of a swage joint may require measuring the inner diameter with a resolution as low as several thousands of an inch. Furthermore, assessing the integrity of a swage joint may require accurately measuring the inner diameter at multiple locations around the inner circumference and/or at a multiple locations along an axial direction of the swage joint which may present challenges when measuring with a bore gauge.

As can be seen, there exists a need in the art for a system and method of measuring the inner diameter of a tube with a high degree of accuracy on a repeatable basis.

SUMMARY

The above-noted needs associated with conventional inspection of tubes or other tubular structures are specifically addressed and alleviated by the present disclosure which provides an apparatus for inspecting a tubular workpiece. The apparatus may include a probe assembly and a rotation mechanism. The probe assembly may include a transducer array positionable adjacent to an inner surface of a tubular workpiece. The probe assembly may be configured to generate transmitted sound waves and receive reflected sound waves. The rotation mechanism may be configured to rotate the probe assembly relative to the tubular workpiece in a manner such that the transducer array passes over the inner surface in a circumferential direction during transmission of the transmitted sound waves.

In a further embodiment, disclosed is an apparatus comprising a probe assembly having a transducer array positionable adjacent to an inner surface of a tubular workpiece in non-contacting relation to the inner surface. The probe assembly may be configured to generate transmitted sound waves toward the inner surface that may impinge on the inner surface. The probe assembly may receive reflected sound waves in response to the transmitted sound waves. The apparatus may further include a rotation mechanism that may be configured to rotate the probe assembly relative to the tubular workpiece in a manner such that the transducer array passes over the inner surface in a circumferential direction during transmission of the transmitted sound waves. In addition, the apparatus may include a container configured to contain a liquid. The container may be sized and configured to immerse the probe assembly and the tube end in the liquid during rotation of the probe assembly relative to the tubular workpiece. The liquid may act as a medium for coupling the transmitted sound waves from the transducer array toward the inner surface of the tubular workpiece.

Also disclosed is a method of inspecting a tubular workpiece. The method may include positioning a probe assembly adjacent to an inner surface of a tubular workpiece, the probe assembly having a transducer array. The method may additionally include generating transmitted sound waves propagating toward the tubular workpiece. Furthermore, the method may include receiving reflected sound waves in response to the transmitted sound waves. The probe assembly may be rotated relative to the tubular workpiece such that the transducer array passes over the inner surface in a circumferential direction during generation of the transmitted sound waves. The method may include detecting a deformation of the tubular workpiece during rotation of the probe assembly.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein.

DETAILED DESCRIPTION

Figure 1:
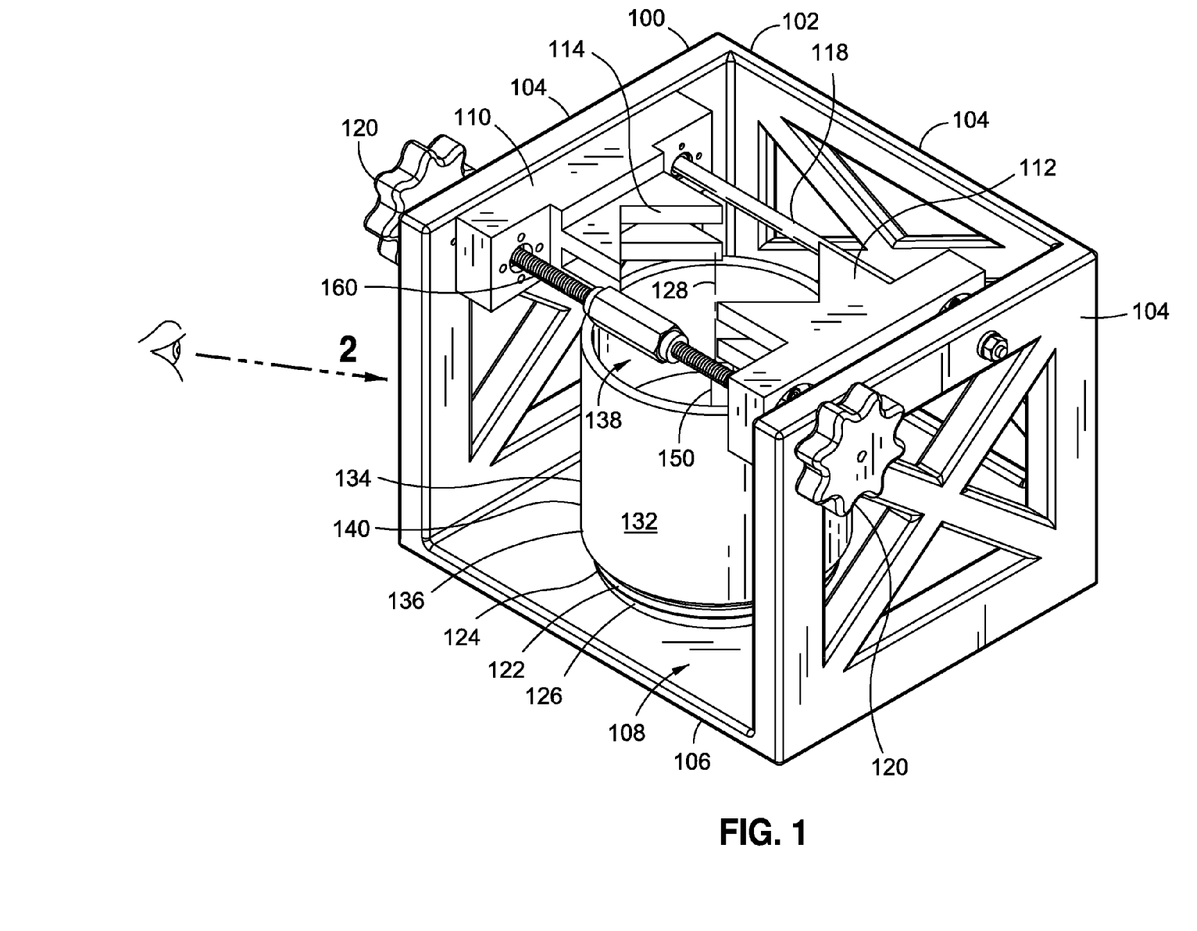
FIG. 1 is a perspective view of an apparatus having a liquid container for immersing an end of a tubular workpiece during ultrasonic inspection using a probe assembly.
Figure 3:
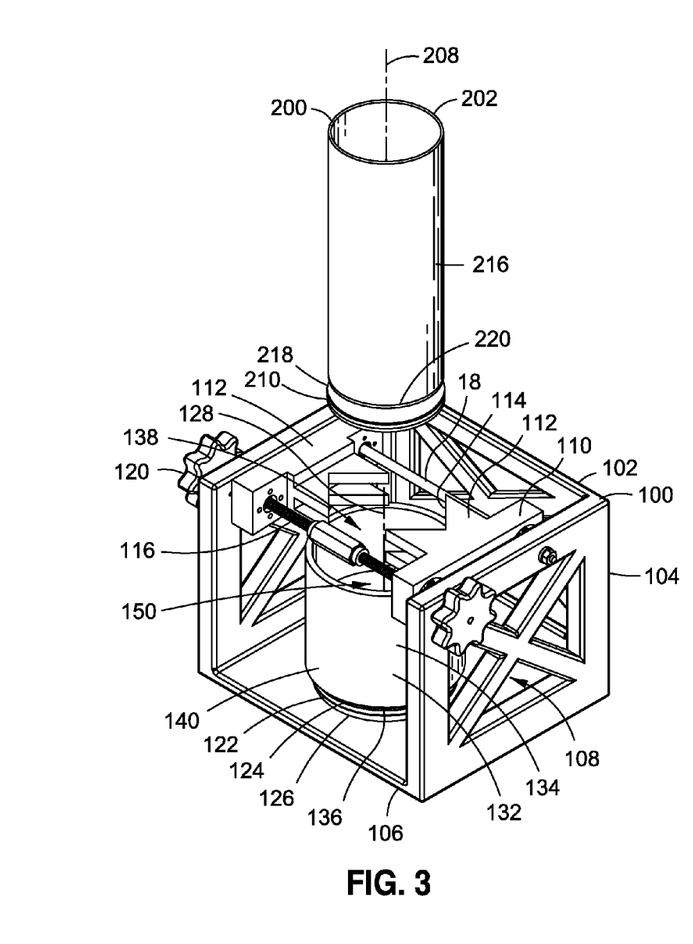
FIG. 3 is a perspective view of the apparatus and a tubular workpiece that may be inspected using the apparatus.
Figure 6:
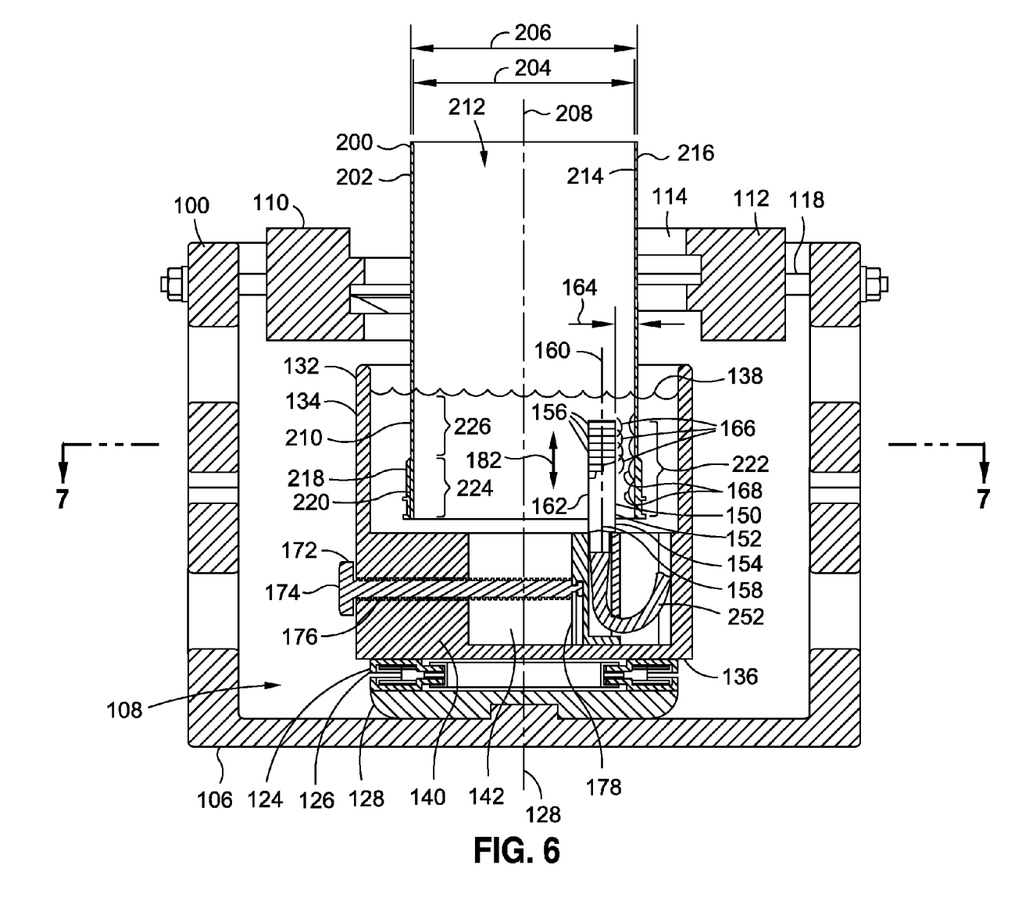
FIG. 6 is a cross-sectional side view of the apparatus and the tubular workpiece.

Referring now to the drawings wherein the showings are for purposes of illustrating various embodiments of the present disclosure, shown in FIG. 1 is an apparatus 100 that may be implemented for use in the ultrasonic inspection of a tubular workpiece 200 (FIG. 3) such as a tube 202 (FIG. 3). For example, the apparatus 100 may be implemented for use in the ultrasonic inspection of a swage joint 220 (FIG. 6) of a fitting 218 (FIG. 6) swaged onto a tube end 210 (FIG. 6) of a tube 202 as illustrated in FIG. 6. However, the apparatus 100 in FIG. 1 may be implemented for ultrasonic inspection of tubular workpieces of any size, shape, and configuration and is not limited to ultrasonic inspection of swage joints on tubes.

In FIG. 1, the apparatus 100 may include a fixture 102. The fixture 102 may include a bottom wall 106 and a plurality of side walls 104 and may be formed of a suitably stiff material such as a metallic material and/or a non-metallic material. Although shown as being formed as a unitary structure, the fixture 102 may be comprised of a plurality of components such as a bottom wall 106 and individual side walls 104 that may be assembled and interconnected by mechanical fastening or adhesive bonding. In this regard, the fixture 102 may be arranged in any configuration that provides a substantially stiff structure for supporting the tubular workpiece 200 (FIG. 6) and probe assembly 150 during ultrasonic testing.

The fixture 102 may include a clamping mechanism 110 configured to fixedly support the tubular workpiece 200 (FIG. 3). The clamping mechanism 110 may allow for vertical positioning of the tubular workpiece 200 (FIG. 3). The clamping mechanism 110 may support the tubular workpiece 200 such that the tube end 210 (FIG. 6) is immersed in liquid 138 (FIG. 6) contained within a container 132 (FIG. 6) mounted within an interior 108 of the fixture 102. The liquid 138 may act as a medium for coupling transmitted sound waves 166 from the probe assembly 150 to an inner surface 214 of a tube end 210 under inspection. As shown in FIG. 6 and described below, the probe assembly 150 may also be immersed in the liquid 138 and positioned within an interior 212 of the tube end 210.

Figure 2:
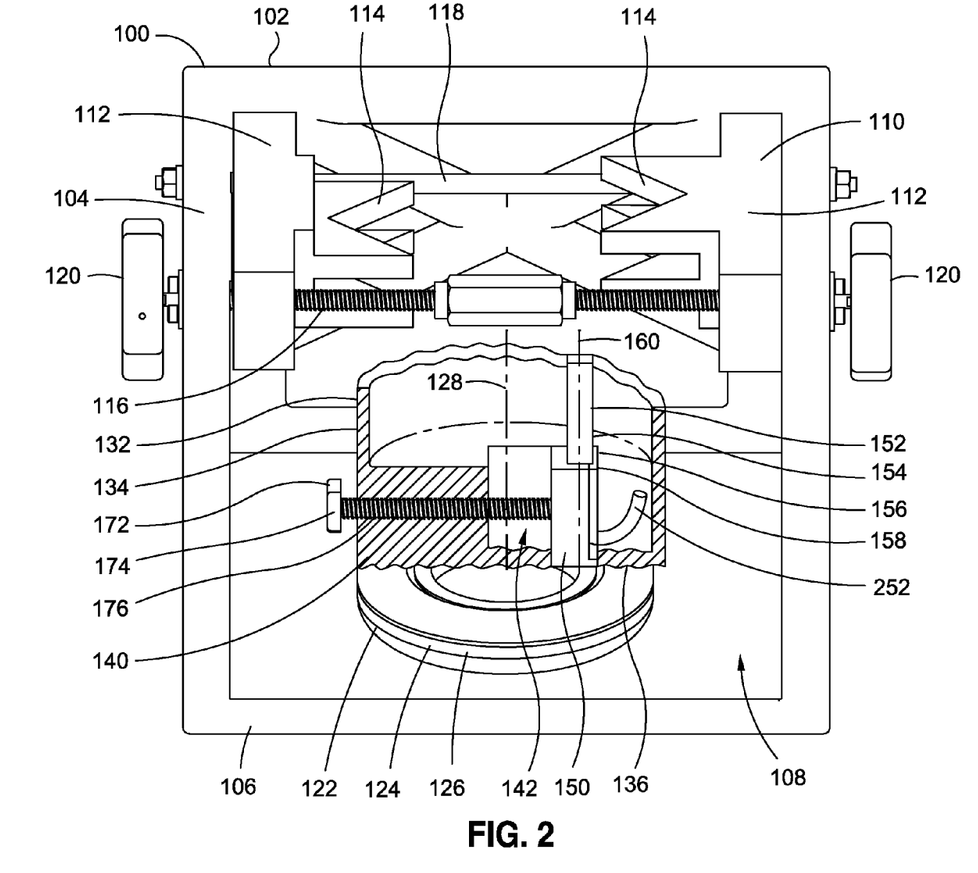
FIG. 2 is an additional perspective view of the apparatus with the liquid container omitted for clarity to illustrate a rotation mechanism for rotation of the probe assembly relative to the tubular workpiece.

In FIG. 2, shown is the apparatus 100 with the container 132 partially cut away to illustrate a rotation mechanism 122 that may be included with the apparatus 100 for rotation of the probe assembly 150 relative to the tubular workpiece 200 (FIG. 6). The probe assembly 150 may comprise a transducer array 152 (FIG. 6) having a plurality of transducer elements 156 (FIG. 6). The probe assembly 150 may be mounted to a bottom portion 140 of the container 132 (FIG. 1). The bottom portion 140 of the container 132 may be mounted on the rotation mechanism 122. The rotation mechanism 122 may comprise a bearing assembly or a turntable 124 having a rotational axis 128. The turntable 124 may be mounted to a base member 126 (FIG. 6) which may be interlocked to the bottom wall 106 of the fixture 102.

The turntable 124 may facilitate rotation of the container 132 and probe assembly 150 relative to the tubular workpiece 200 (FIG. 7) in a manner such that the transducer array 152 moves along a circumferential direction 180 (FIG. 7) passing over an inner surface 214 (FIG. 7) of the tube end 210 (FIG. 7) as the transducer elements 156 generate transmitted sound waves 166 (e.g., ultrasonic sound waves—FIG. 7) as described in greater detail below. In this manner, the probe assembly 150 may ultrasonically inspect a swage joint 220 (FIG. 6) of the fitting 218 to the tube end 210. For example, the probe assembly 150 may ultrasonically inspect the tube end 210 (FIG. 6) to measure an increase in the diameter of the inner surface 214 (FIG. 6) along a joint section 224 (FIG. 6) of the tube 202 relative to a non joint section 226 (FIG. 6) of the tube 202. If the diameter of the inner surface 214 falls within a predetermined dimensional range, the fitting 218 may be verified as being correctly swaged onto the tube end 210.

Although FIG. 2 illustrates the rotation mechanism 122 as rotating the container 132 (FIG. 1) and the probe assembly 150 while the tubular workpiece 200 is maintained in a stationary position, the apparatus 100 may optionally be provided in an alternative embodiment (not shown) wherein the tubular workpiece 200 is rotated while the probe assembly 150 is maintained in a stationary position. In a further embodiment not shown, the apparatus 100 may be arranged such that both the probe assembly 150 and the tubular workpiece 200 are configured to rotate in opposite directions relative to one another. Although not shown, the apparatus 100 may also be provided in an embodiment wherein the container 132 and the tubular workpiece 200 are stationary and the probe assembly 150 rotates. In this regard, the apparatus 100 may be provided in any embodiment that facilitates rotation of the probe assembly 150 relative to the tube end 210 in a manner such that the probe assembly 150 passes over the tube end 210 along a circumferential direction 180 while transmitted sound waves 166 are emitted from the probe assembly 150 as described in below.

In FIG. 2, the apparatus 100 may include a radial adjustment mechanism 172 for adjusting the radial location 178 of the probe assembly 150 relative to the inner surface 214 (FIG.

6) of a tube end 210 (FIG. 6). For example, the radial adjustment mechanism 172 may comprise a rotatable thumb screw 174 having a shaft 176 that may extend through the bottom portion 140 of the container 132. The thumb screw 174 may be exteriorly accessible on the container side wall 134. The shaft 176 may be threadably engaged to the bottom portion 140 of the container 132. An end of the shaft 176 may be coupled to the probe assembly 150. The probe assembly 150 may be slideable along a slot 142 that may be formed in the bottom portion 140 of the container 132.

Rotation of the thumb screw 174 may result in the movement of the probe assembly 150 in a radial direction within the slot 142. In this manner, the thumb screw 174 may provide a means for adjusting the radial location 178 of the probe assembly 150 to accommodate tubes of different diameters. In this regard, the thumb screw 174 may provide a means for accurately positioning the probe assembly 150 at a predetermined distance 164 from the inner surface 214 (FIG. 6) of the tube end 210. The thumb screw 174 may also provide a means for fine tuning the distance 164 (FIG. 6) from the transducer elements 156 (FIG. 6) to the inner surface 214 of the tube end 210. Adjustment of the distance 164 between the transducer elements 156 in the inner surface 214 may provide a means for improving the resolution of the probe assembly 150 as described in greater detail below. Although the radial adjustment mechanism 172 is illustrated and described herein as a manually adjustable thumb screw 174, the radial adjustment mechanism 172 may be provided in any one of a variety of different sizes, shapes and configurations and is not limited to a thumb screw 174 embodiment.

Figure 4:
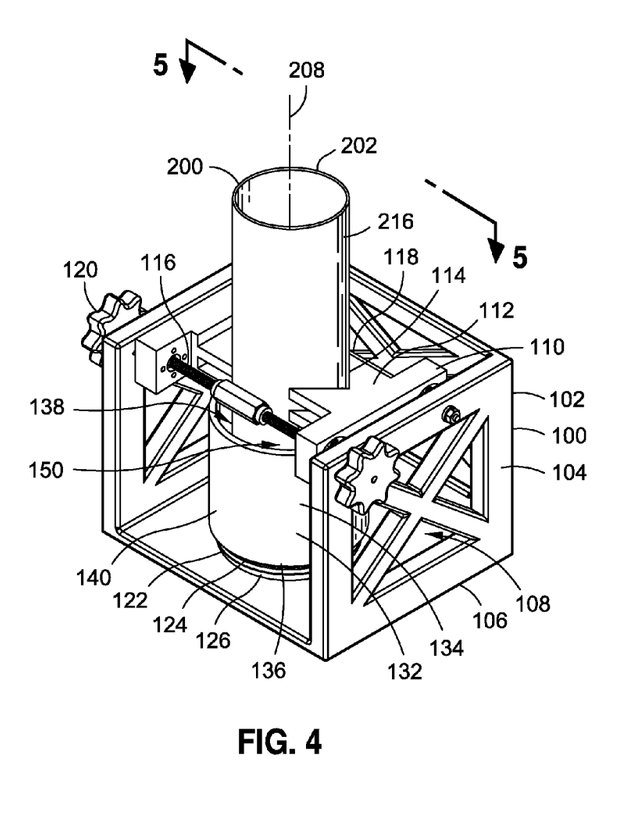
FIG. 4 is a perspective view of the apparatus with the tubular workpiece clamped to the apparatus using a clamping mechanism.

Referring to FIGS. 3-4, shown are perspective views of the apparatus 100 and illustrating the operation of the clamping mechanism 110 in an embodiment. The clamping mechanism 110 may be configured to support the tubular workpiece 200 in a fixed position. The tubular workpiece 200 may include a workpiece longitudinal axis 208. FIG. 3 shows the tubular workpiece 200 above the fixture 102 prior to being clamped in position by the clamping mechanism 110. The clamping mechanism 110 may include an opposing pair of jaws 112. The jaws may be mounted on a pair of generally parallel rods extending between a pair of the fixture 102 side walls 104. At least one of the rods may comprise a threaded rod 116. Another of the rods may comprise a non-threaded rod 118. At least one side of each one of the jaws 112 may be engaged to one of the rods 116, 118.

The jaws 112 may be laterally movable in opposing directions. In an embodiment, the jaws 112 may be configured to move in substantially equal amounts toward and away from one another. The clamping mechanism 110 may include one or more thumb wheels 120 mounted to one or both sides of the threaded rod 116. Each one of the jaws 112 may be provided with a V-shaped notch 114. Rotation of one or both of the thumb wheels 120 may provide a means to adjust the spacing between the jaws 112 such that the notches 114 may accommodate tubular workpieces 200 having different outer diameters.

FIG. 4 shows the tubular workpiece 200 clamped in position by the clamping mechanism 110. The clamping mechanism 110 may be configured to clamp the tubular workpiece 200 such that the workpiece longitudinal axis 208 is oriented generally parallel to or is approximately coincident with the rotational axis 128 (FIG. 2) of the rotation mechanism 122. In this regard, the clamping mechanism 110 may provide a means for centering the tube end 210 (FIG. 3) with the rotational axis 128 of the rotation mechanism 122. The jaws 112 of the clamping mechanism 110 may be configured to clamp the tubular workpiece 200 such that the workpiece longitudinal axis 208 at the tube end 210 is substantially coincident with the rotational axis 128 of the rotation mechanism 122.

Figure 5:
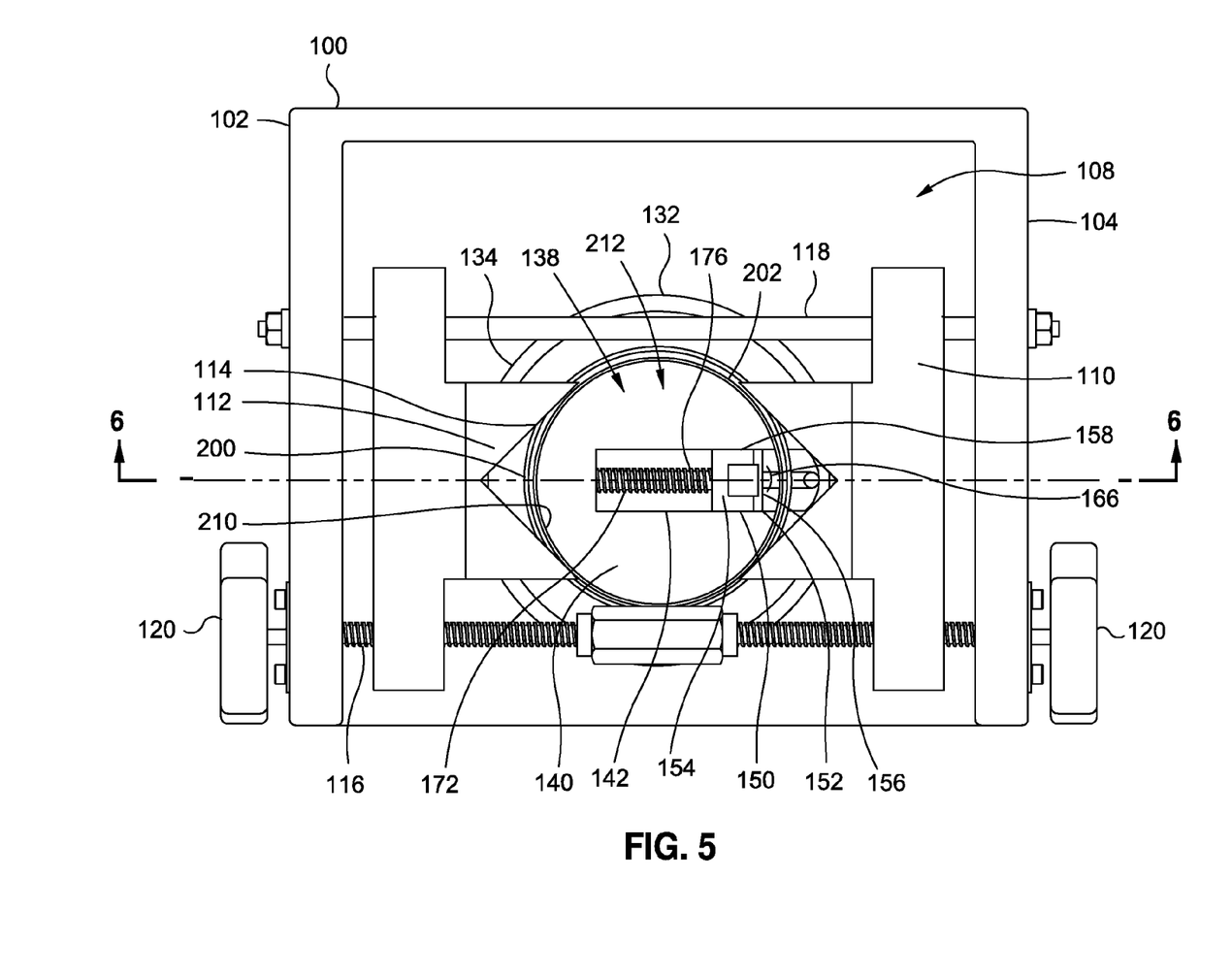
FIG. 5 is a top view of the apparatus with the tubular workpiece clamped in position.

FIG. 5 is a top view of the apparatus 100 having a tubular workpiece 200 clamped between the jaws 112 of the clamping mechanism 110. The tubular workpiece 200 is shown being generally centered relative to the rotational axis 128 (FIG. 2) of the rotation mechanism 122. However, the apparatus 100 as disclosed herein is not limited to inspecting substantially straight tubular workpieces 200 but may advantageously be implemented for inspecting workpieces that are non-straight (not shown) or which are slightly curved (not shown) along a lengthwise direction of such workpieces. For such non-straight or slightly curved workpieces, the thumb wheels 120 may be adjusted such that the jaws 112 are biased toward one side of the fixture 102 by an amount that results in the tube end 210 to be centered with the rotational axis 128 of the rotation mechanism 122 (i.e., centered within the container 132) (FIG. 3). In this manner, the probe assembly 150 may be clamped in position such that the tube end 210 is generally centered and the probe assembly 150 maintains a substantially constant distance 164 (FIG. 6) from the inner surface 214 (FIG. 6) as the probe assembly 150 rotates relative to the tubular workpiece 200.

FIG. 6 is a cross-sectional side view of the apparatus 100 with the tubular workpiece 200 clamped in position by the clamping mechanism 110 and the tube end 210 immersed in liquid 138 contained within the container 132. As indicated above, the probe assembly 150 may comprise a transducer array 152 having a plurality of transducer elements 156. In an embodiment, the transducer elements 156 may be arranged in a linear array 154 and may be mounted in an array case 158. The probe assembly 150 may be positioned in relatively close proximity to the inner surface 214 of the tube end 210 such that the transducer elements 156 are in non-contacting relation to the inner surface 214. The transducer elements 156 may be arranged at substantially equal distances from one another along the length of the linear array 154. The linear array 154 may be linear in the sense that the transducer elements 156 may be oriented in a single column in a generally straight line. However, the probe assembly 150 may include one or more vertical columns (not shown) of transducer elements 156 arranged in a linear array 154 and is not limited to a single column of transducer elements 156.

Figure 10:
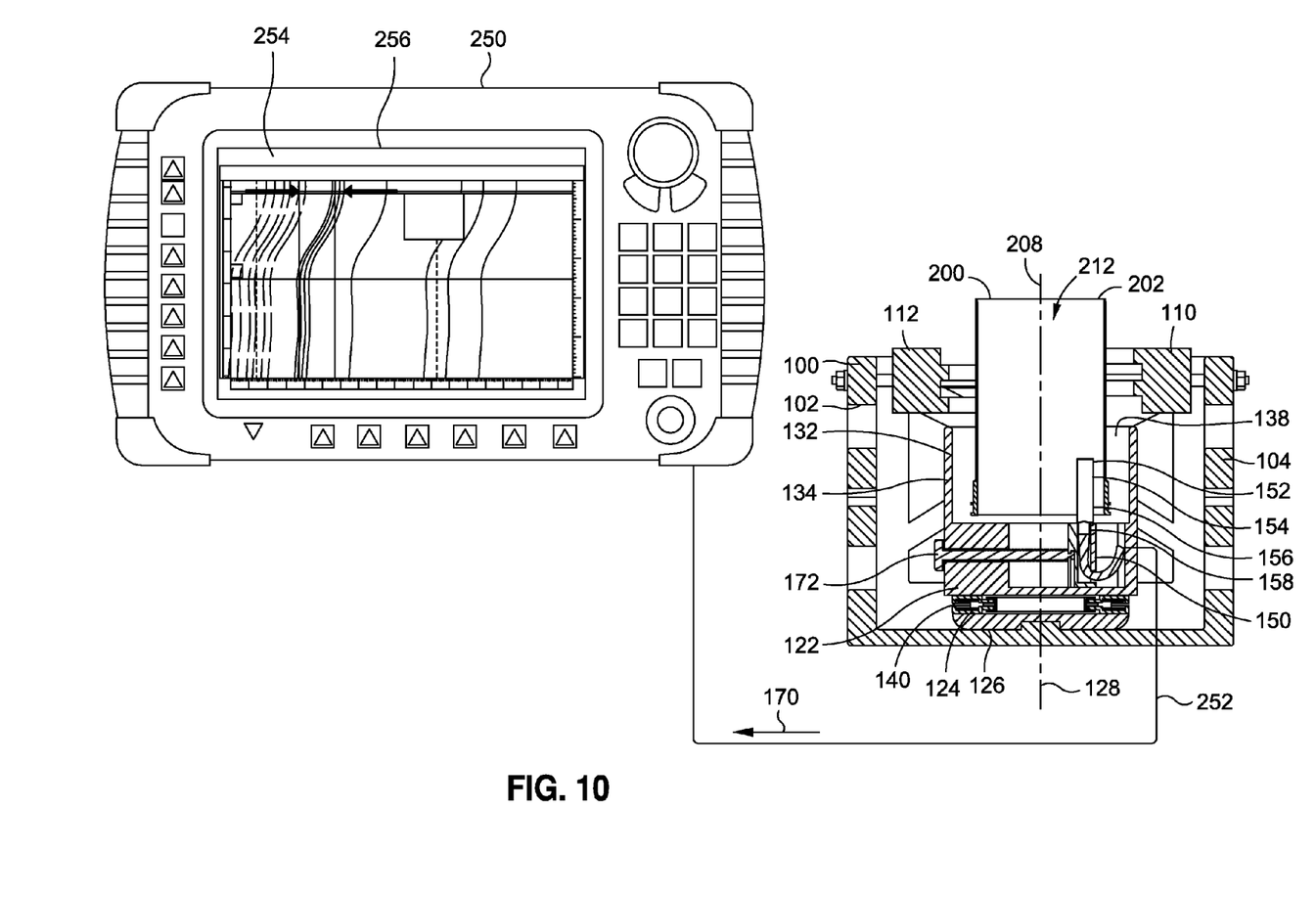
FIG. 10 is a diagram of the apparatus wherein the probe assembly is communicatively coupled to a computer.

Each one of the transducer elements 156 may generate ultrasonic sound waves defined herein as transmission sound waves 166. The transducer elements 156 may be oriented such that the transmission sound waves 166 are generally directed toward the inner surface 214 of the tube end 210. The transmission sound waves 166 may initially impinge on an inner surface 214 of the tube end 210. A portion of the transmission sound waves 166 may reflect off of the inner surface 214 of the tube end 210 and may return toward the probe assembly 150 as reflected sound waves 168. Other portions of the transmitted sound waves 166 may propagate into the tube end 210 and into the fitting 218. Reflected sound waves 168 may be reflected at the interface between the tube end 210 and the fitting 218 and/or at an outer surface of the fitting 218 and/or at other portions of the area under inspection 222. The probe assembly 150 may be configured to receive the reflected sound waves 168 and generate electrical signals 170 (FIG. 10) representative thereof. Such electrical signals 170 may be delivered to a computer 250 (FIG. 10) as described below for processing and/or displaying as a graphical image 256 (FIG. 10) on a display device 254 (FIG. 10).

Referring still to FIG. 6, the apparatus 100 may be configured such that the linear array 154 of transducer elements 156 are activated in a preprogrammed sequence. In an embodiment, sets (not shown) of the transducer elements 156 may be activated in a sequential manner. For example, for a linear array 154 having fourteen (14) (or other arbitrary quantity) transducer elements 156 arranged in a generally straight line, predetermined sets of the transducer elements 156 may be activated concurrently. For example, in a three-channel linear array (not shown), each one of the channels (not shown) may activate a set of twelve (12) of the transducer elements 156 concurrently. A first channel may include transducer elements 1-12, a second channel may include transducer elements 2-13, and third channel may include transducer elements 3-14. The concurrent activation of sets of twelve (12) transducer elements 156 (or other arbitrary quantity) may increase the magnitude of the ultrasonic energy impinging on the tubular workpiece 200 and may increase the resolution of ultrasonic inspection relative to a mode of operation where individual transducer elements are separately activated.

In FIG. 6, the linear array 154 may have an array longitudinal axis 160. Advantageously, the apparatus 100 may be configured such that the array longitudinal axis 160 may be maintained in generally parallel relation to the rotational axis 128 of the rotation mechanism 122 (FIG. 2) during rotation of the probe assembly 150 relative to the tubular workpiece 200. The linear array 154 may also be oriented relative to the tubular workpiece 200 such that the array longitudinal axis 160 is maintained substantially parallel to the workpiece longitudinal axis 208 during rotation of the probe assembly 150 relative to the tubular workpiece 200. The linear array 154 may be provided in an array length 162 such that the transducer elements 156 extend along a substantial length of the area under inspection 222. In this regard, the transducer elements 156 may be spaced along the joint section 224 and along at least a portion of a non joint section 226 of the tube end 210.

Figure 7:
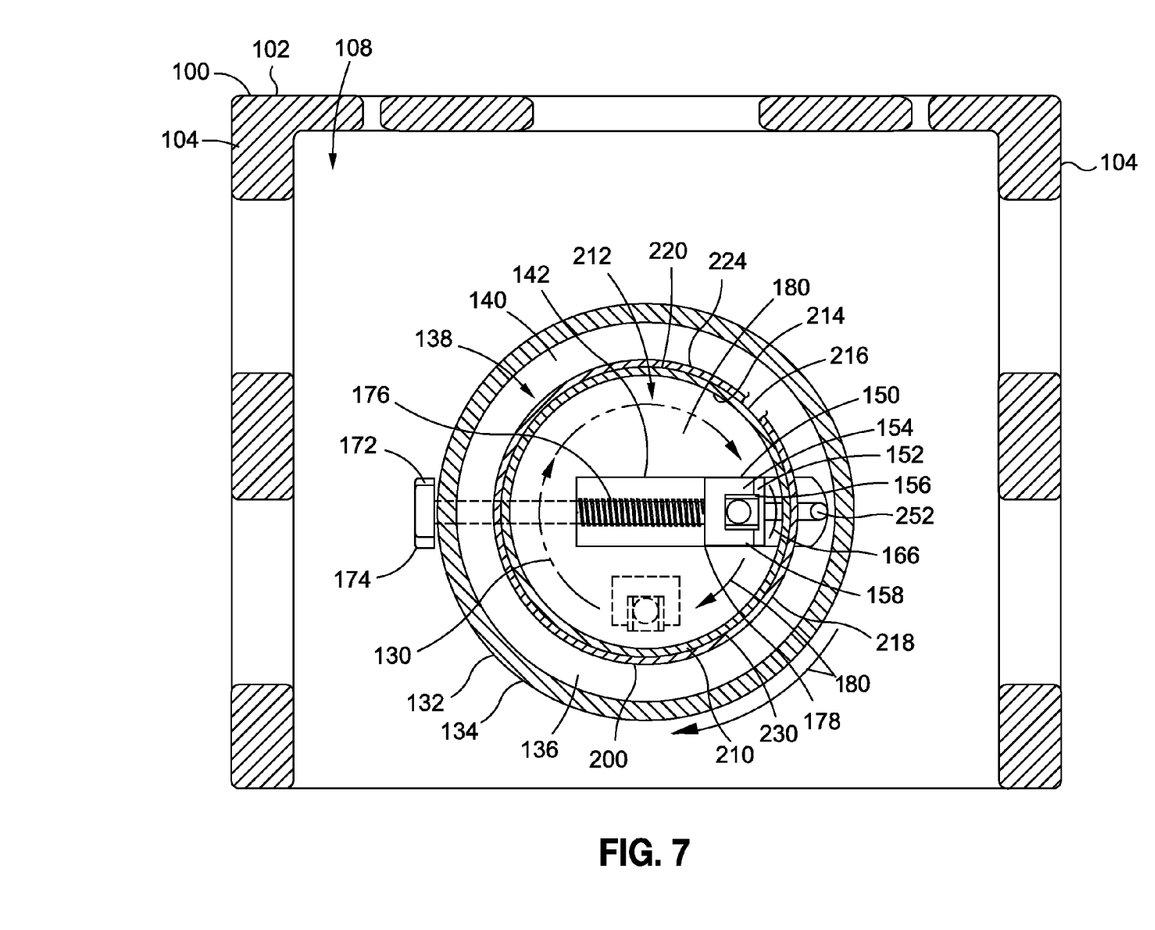
FIG. 7 is a cross sectional top view of the apparatus and the tubular workpiece.

FIG. 7 is a cross sectional plan view of the apparatus 100 showing the probe assembly 150 mounted to the container bottom portion 140. The probe assembly 150 may be positioned within the interior 212 of the tube end 210 and may be rotated along a direction of rotation 130. As indicated above, the probe assembly 150 may be configured to be radially movable along the slot 142 in the container bottom portion 140 by adjusting the radial adjustment mechanism 172. Although a single probe assembly 150 is shown in FIG. 7, the apparatus 100 may include two or more probe assemblies (not shown). For example, the apparatus 100 may include two or more probe assemblies radially spaced apart from one another. For example, the apparatus 100 may include two probe assemblies that may be diametrically-opposed from one another.

It should also be noted that the apparatus 100 is not limited to having a single probe assembly 150 operating in a pulse-echo mode of operation wherein the single probe assembly 150 generates and receives ultrasonic sound waves. For example, in an embodiment not shown, the apparatus 100 may be configured in an attenuation mode wherein the apparatus 100 may include a probe assembly on an interior of a tube end and a receiver assembly (not shown) on an exterior of the tube end opposite the probe assembly. In an attenuation mode of operation, a receiver assembly may receive ultrasonic waves that emitted by a probe assembly and which propagate through a tube end and a fitting. The receiver assembly may generate electrical signals that may be representative of the ultrasonic waves propagating through the tube end and the fitting. Such electrical signals may be delivered to a computer as described below for processing and/or displaying as a graphical image on a display device.

In FIG. 7, the probe assembly 150 may be configured such that the transducer array 152 may be positioned in relatively close proximity to the inner surface 214 of the tube end 210. For example, as described above, the radial adjustment mechanism 172 or thumb screw 174 may be manually rotated to adjust the radial location 178 of the transducer elements 156 to be within a desired distance 164 (FIG. 6) of the inner surface 214 of the tube end 210. The apparatus 100 may be configured such that the transducer elements 156 are maintained at a substantially constant distance 164 from the inner surface 214 of the tube end 210 during a 360° rotation of the probe assembly 150 relative to the tube end 210. Advantageously, by maintaining a substantially constant distance 164 between the transducer elements 156 and the inner surface 214 during relative rotation of the probe assembly 150, the accuracy and consistency of the ultrasonic inspection may be improved.

In FIG. 7, the transducer elements 156 may be arranged such that the transmitted sound waves 166 impinge on the inner surface 214 approximately normal or perpendicular to the inner surface 214. However, the transducer elements 156 may be oriented in any arrangement and are not limited to an arrangement resulting in impingement of the transmitted sound waves 166 substantially normal to the inner surface 214. In an embodiment, the transducer elements 156 may be configured to generate ultrasonic waves at a predetermined frequency dependent upon the size of the deformation 230 that is required to be detected. For example, the transducer elements 156 may be configured to generate transmitted sound waves 166 at a relatively high frequency to improve the sensitivity of the ultrasonic inspection and effectively reduce the size of a feature (e.g., deformation 230) that may be reliably detected.

In this regard, the probe assembly 150 may be configured to provide a desired level of sensitivity or resolution of ultrasonic inspection by exciting the transducers elements 156 at a predetermined frequency. The sensitivity or resolution of ultrasonic inspection may be based on the inverse relationship of frequency to wavelength. The frequency may be equal to the velocity of sound in water (e.g., approximately 4,800 ft/sec) divided by the wavelength. In ultrasonic inspection, the smallest size of a feature (e.g., a deformation) that may be detected must be at least as large as one-half the wavelength of the operating frequency. To facilitate detection of deformations on the order of several thousands of an inch, the transducer elements 156 (FIG. 7) may be configured to generate transmitted sound waves 166 at a frequency of at least approximately 10 megahertz (MHz) which may correspond to a wavelength of approximately 0.0058 inch. At 10 MHz, the probe assembly 150 may have a sensitivity of approximately 0.0029 inch which may facilitate reliable measurement of diameter increases for verifying the integrity of a swage joint 220 (FIG. 7). As may be appreciated, the apparatus 100 is not limited to excitation of the transducer elements 156 at 10 MHz. In this regard, the apparatus 100 may be configured such that the transducer elements 156 may be excited at any desired frequency to provide a desired level of sensitivity and resolution capability.

Figure 8:
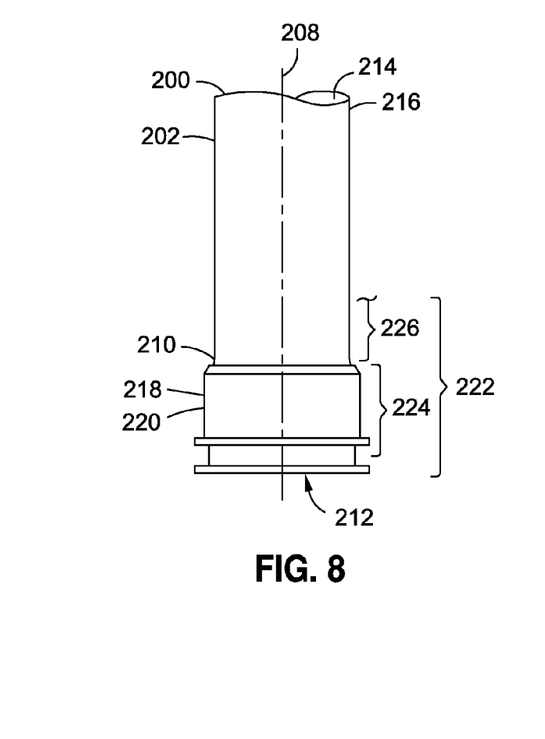
FIG. 8 is a side view of a tubular workpiece having a fitting swaged onto a tube end.
Figure 9:
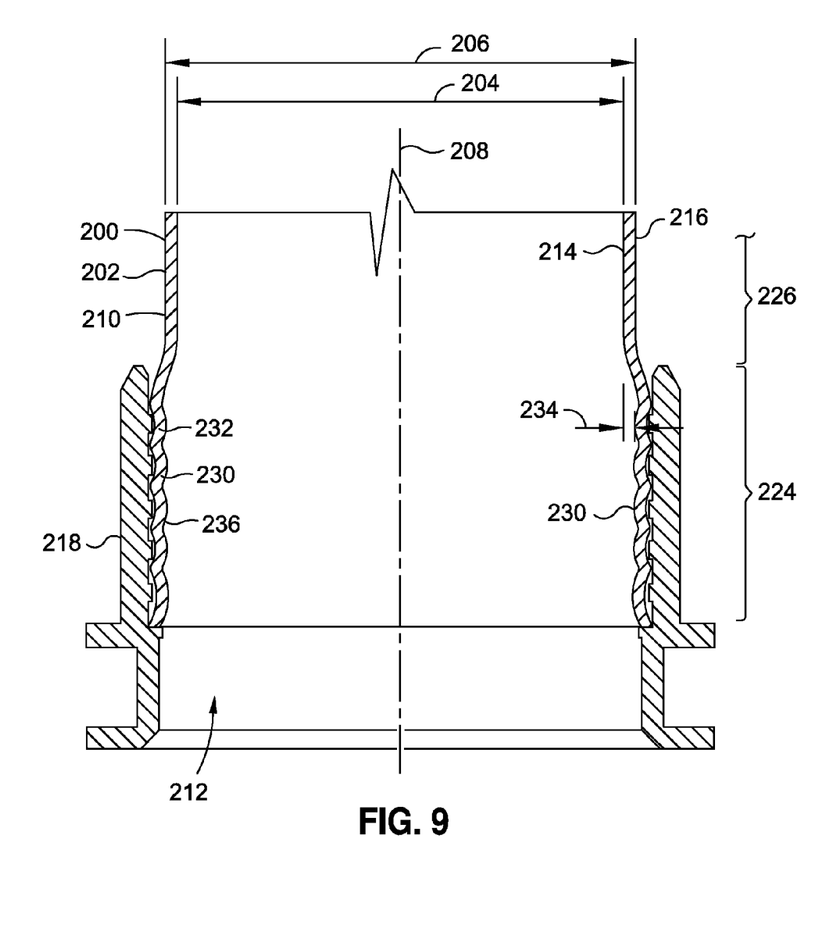
FIG. 9 is an enlarged cross sectional view of the tube end and illustrating deformation of the tube end along a joint section of the swage joint.

Referring to FIG. 8-9, shown is a portion of a tubular workpiece 200 having a fitting 218 mounted on a tube end 210. FIG. 8 illustrates the workpiece longitudinal axis 208 extending lengthwise along the tubular workpiece 200. As shown in FIG. 9, the tubular workpiece 200 has a nominal outer diameter 206 and a nominal inner diameter 204 along a non-joint section 226 of the tubular workpiece 200. A fitting 218 is swaged onto the tube end 210 at a joint section 224 where the tube end 210 is plastically deformed such that the material of the tube end 210 is expanded into circumferential grooves or other surface features formed on the interior circumference of the fitting 218. The expansion of the tube end 210 may result in an increase in the diameter of the tube end 210 along the joint section 224 relative to the diameter at a non-joint section 226 of the tube 202.

In an embodiment disclosed herein, the probe assembly 150 (FIG. 6) may be provided in a length that spans the joint section 224 and at least a portion of the non joint section 226 of the tube 202. The joint section 224 and the portion of the non joint section 226 may comprise the area under inspection 222 along an axial direction 182 (FIG. 6) of the tube 202. Rotation of the probe assembly 150 relative to the tubular workpiece 200 may facilitate ultrasonic inspection of the tube end 210 in a circumferential direction 180 (FIG. 7). For example, the probe assembly 150 may be rotated approximately 360° to ultrasonically examine a substantial entirety of the inner circumference of the tube end 210.

During ultrasonic inspection, the tubular workpiece 200 may be immersed within a medium such as liquid 138 (FIG. 6) contained within the container 132 (FIG. 6). In an embodiment, the container 132 (FIG. 7) has a container bottom wall 136 (FIG. 7) and a container side wall 134 (FIG. 7) having a cylindrical configuration. However, the container 132 may be provided in any configuration without limitation and is not limited to a cylindrical configuration. The liquid 138 may couple the transmitted sound waves 166 (FIG. 6) from the transducer elements 156 (FIG. 6) to the tubular workpiece 200 in the area under inspection 222 (FIG. 6). In an embodiment, the liquid 138 may comprise water which may minimize clean-up of the workpiece following inspection. The use of water as the medium may also avoid contamination that may be associated with other mediums such as oil. However, the liquid 138 may be provided as any type of fluid and is not limited to water.

FIG. 10 is a block diagram illustrating the probe assembly 150 communicatively coupled to a computer 250 via a data/power line 252. The computer 250 may be configured to regulate the operation of the apparatus 100 including the rotation mechanism 122 and the probe assembly 150. For example, the computer 250 may facilitate activation of the linear array 154 of transducer elements 156 in a sequential or phased manner as described above or in a non-sequential manner. In addition, the computer 250 may control the excitation voltage that may be applied to the transducer elements 156 to generate transmission sound waves 166 (i.e., ultrasonic sound waves) at a desired frequency. Furthermore, the computer 250 may be configured to process the reflected sound waves 168 (FIG. 6) which may be provided to the computer 250 as electrical signals 170 from the probe assembly 150 via the data/power line 252.

Figure 11:
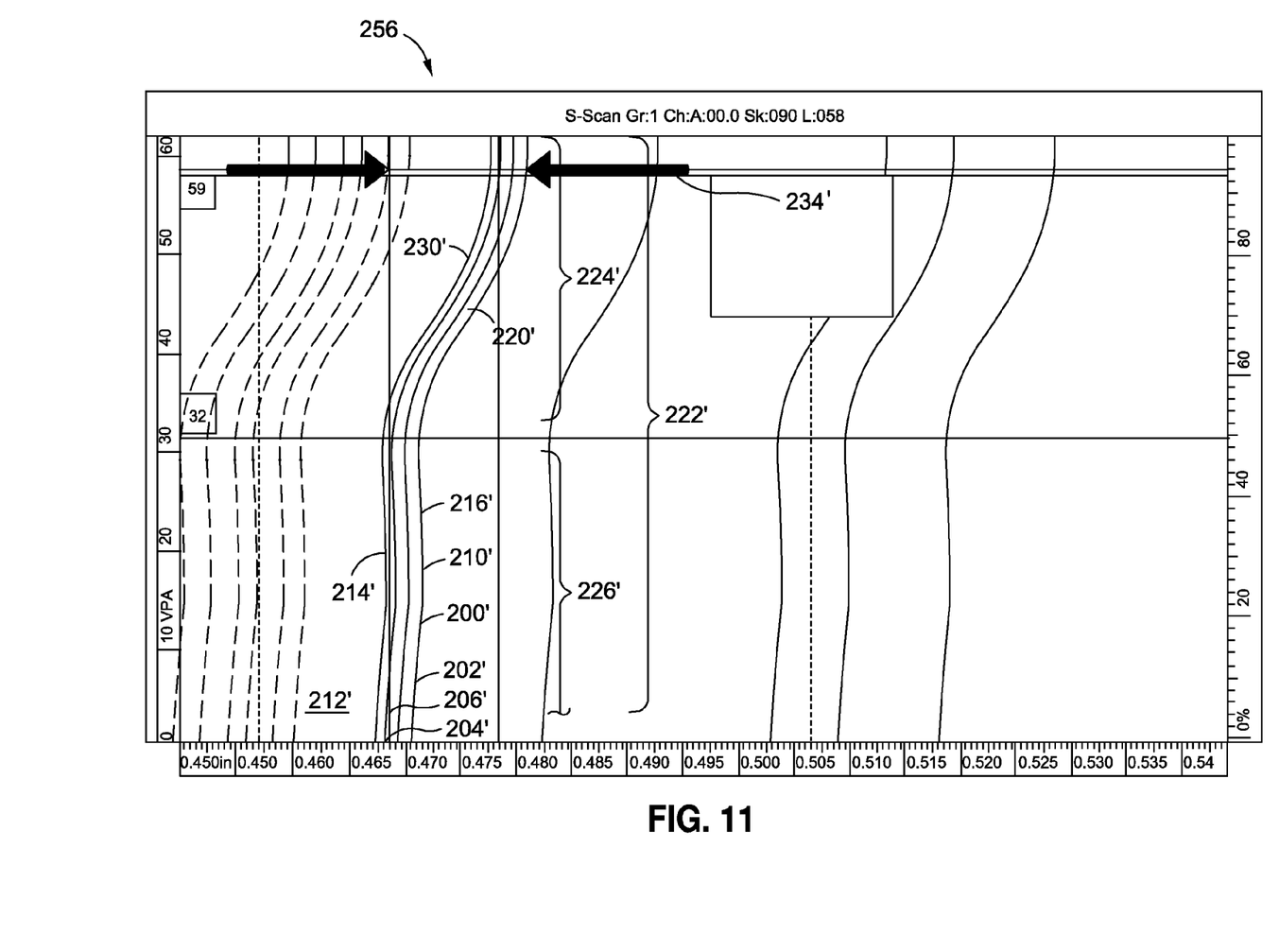
FIG. 11 is an illustration of a graphical image of the tube end showing deformation measured by the probe assembly during ultrasonic inspection using the apparatus.

FIG. 11 illustrates a graphical image 256 displayed on a display device 254 (FIG. 10) that may be included with the computer 250 (FIG. 10). As indicated above, the probe assembly 150 (FIG. 10) may generate electrical signals 170 (FIG. 10) representative of the reflected sound waves 168 (FIG. 7). The display device 254 may receive the electrical signals 170 from the probe assembly 150 and may generate the graphical image 256 representative of deformation 230' of the tube end 210'. For example, the graphical image 256 may be representative of the shape and size (i.e., diameter) of the inner surface 214' at the swage joint 220' along the joint section 224' and non joint section 226' of the area under inspection 222'. The graphical image 256 may be generated in real time during rotation of the probe assembly 150 relative to the tubular workpiece 200' while the probe assembly 150 is generating the transmitted sound waves 166 (FIG. 6) and receiving the reflected sound waves 168 (FIG. 6). The graphical image 256 may also be generated following rotation of the probe assembly 150 relative to the tubular workpiece 200'. In an embodiment, the computer 250 and display device 254 may facilitate the characterization of the deformation 230' of the tube end 210' in the tubular workpiece 200' to ascertain the integrity of a swage joint 220'.

In FIG. 11, the display device 254 (FIG. 10) may display a graphical image 256 representing a difference 234' in diameter of the inner surface 214' along the joint section 224' of the tube end 210' relative to a nominal inner diameter 204' of the tube at a non joint section 226'. The display device 254 may also be configured to graphically illustrate one or more anomalies (not shown) that may be associated with the tubular workpiece 200'. In an embodiment, the probe assembly 150 (FIG. 10) may be configured to measure a thickness variation (not shown) of the tube end 210' and/or the fitting (not shown) along at least one of an axial direction 182 (FIG. 7) and a circumferential direction 180 (FIG. 8) of the tube end 210'. The computer 250 may be configured to store data representative of the ultrasonic inspection of the tube end 210'. The display device 254 may also be configured to render or display information in non-graphical form such as text data characterizing a deformation 230' or an anomaly (not shown) that may be associated with the tubular workpiece 200'.

Figure 12:
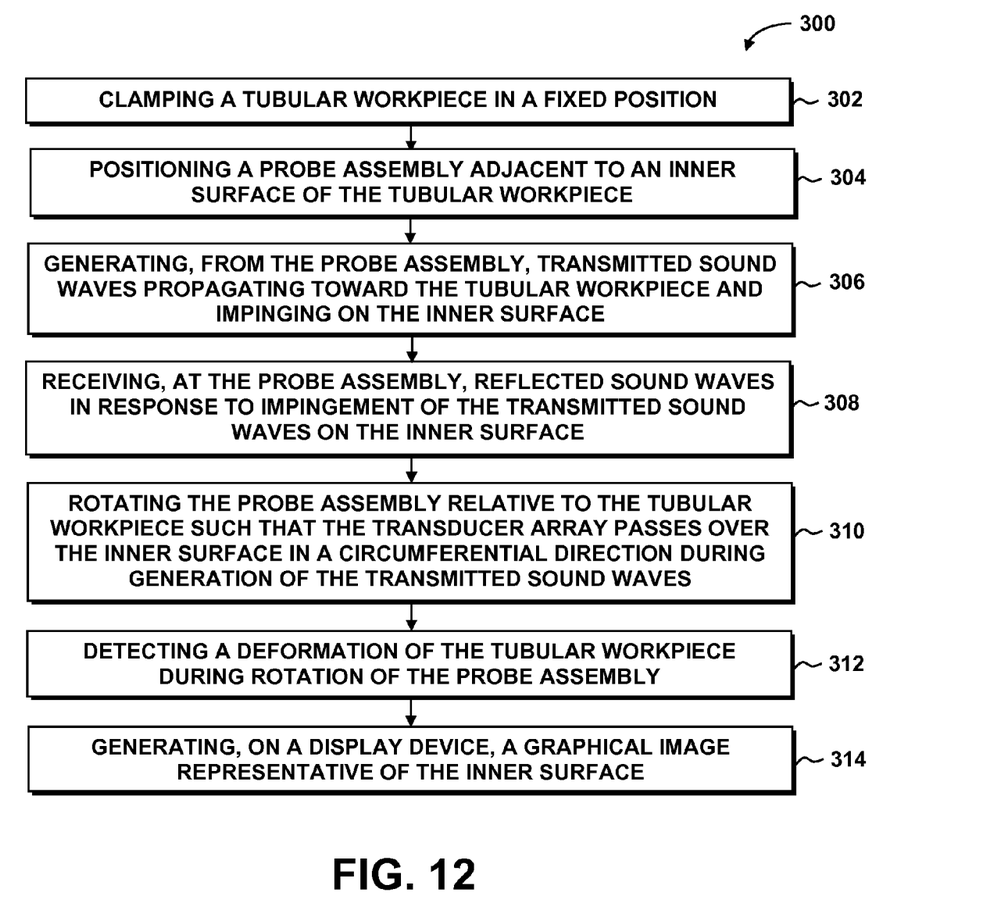
FIG. 12 is a flow diagram having one or more operations that may be included in a method of inspecting a tubular workpiece.

FIG. 12 is a flow chart illustrating one or more operations that may be included in a method 300 of inspecting a tubular workpiece 200 (FIG. 6). Step 302 of the method 300 may include clamping a tubular workpiece 200 in a fixed position such that the tube end 210 (FIG. 6) is maintained in substantially centered relation to a rotational axis 128 (FIG. 6) of the probe assembly 150 (FIG. 6) during rotation thereof. As described above, the tubular workpiece 200 may include the tube end 210 having the fitting 218 (FIG. 6) swaged to a circumferential outer surface 216 (FIG. 6) of the tube end 210 at a joint section 224 (FIG. 6) of the tube end 210.

Step 304 of the method 300 of FIG. 12 may include positioning a probe assembly 150 within an interior 212 of the tubular workpiece 200 and adjacent to the inner surface 214 as shown in FIG. 6. The radial location 178 of the probe assembly 150 may be adjusted relative to the rotational axis 128 using the radial adjustment mechanism 172. For example, the radial adjustment mechanism 172 (FIG. 6) may comprise a thumb screw 174 (FIG. 6) that may facilitate radial adjustment of the probe assembly 150 to position the probe assembly 150 at a predetermined distance 164 (FIG. 6) from the inner surface 214 (FIG. 6). In an embodiment, the method 300 may include immersing the probe assembly 150 and the area under inspection 222 in a medium such as a liquid 138 (e.g., water). The liquid 138 may couple the transmitted sound waves 166 from the probe assembly 150 to the inner surface 214 which may improve the efficiency of ultrasonic inspection.

Step 306 of the method 300 of FIG. 12 may include generating transmitted sound waves 166 (FIG. 6) using the transducer elements 156 of the probe assembly 150. The transmitted sound waves 166 may propagate toward the tubular workpiece 200 and may impinge on the inner surface 214 of the tube end 210 and the fitting 218. Step 306 may include determining a minimum detectable size of an anomaly 232 (FIG. 9) for detection by the apparatus 100 and exciting the transducer elements 156 at a frequency having a half-wavelength that is no larger than the minimum detectable size. For example, as indicated above, for measuring deformation 230 of no smaller than approximately 0.003 inch, the transducer elements 156 may be excited by applying voltage such that the transmitted sound waves 166 have a frequency of no less than approximately 10 MHz. However, the transducer elements 156 may be excited any frequency, without limitation.

Step 308 of the method 300 of FIG. 12 may include receiving reflected sound waves 168 (FIG. 6) at the probe assembly 150 (FIG. 6) in response to impingement of the transmitted sound waves 166 (FIG. 6) on the tube end 210 (FIG. 6). In an embodiment, the probe assembly 150 may operate in a pulse-echo mode where the probe assembly 150 both transmits and receives ultrasonic sound waves. However, the apparatus 100 (FIG. 6) may be provided in an embodiment having a probe assembly 150 on an interior 212 of the tube end 210 and a receiving assembly (not shown) on an exterior of the tube end 210, or vice versa.

Step 310 of the method 300 of FIG. 12 may include rotating the probe assembly 150 (FIG. 7) relative to the tubular workpiece 200 (FIG. 7) such that the transducer array 152 (FIG. 7) passes over the inner surface 214 (FIG. 7) in a circumferential direction 180 (FIG. 7). Relative rotation of the probe assembly 150 and the tubular workpiece 200 may be performed during generation of the transmitted sound waves 166 (FIG. 7) and during receipt of the reflected sound waves 168 (FIG. 7). The probe assembly 150 and/or the tubular workpiece 200 may be rotated about a rotational axis 128 (FIG. 6) of the rotation mechanism 122 (FIG. 6). For example, the tubular workpiece 200 may be rotated and the probe assembly 150 may be stationary, or the tubular workpiece 200 may be stationary and the probe assembly 150 may be rotated. The transmitted sound waves 166 and the reflected sound waves 168 may be respectively generated and received at the probe assembly 150 on a substantially continuous basis during rotation of the probe assembly 150 relative to the tubular workpiece 200.

Step 312 of the method 300 of FIG. 12 may include detecting a deformation 230 (FIG. 9) of the tubular workpiece 200 (FIG. 9) during rotation of the probe assembly 150. For example, detection of a deformation 230 may include measuring the diameter of the inner surface 214 (FIG. 9) relative to a nominal inner diameter 204 (FIG. 9) of the tube as was indicated above. Step 312 may also include identifying one or more anomalies that may exist in the tubular workpiece 200 from a graphical image 256 (FIG. 10) representative of the received reflected sound waves 168. In an embodiment, the probe assembly 150 may provide a means for measuring a thickness variation 236 (FIG. 9) of the tube end 210 and/or the fitting 218 along at least one of an axial direction 182 and a circumferential direction 180 of the tube end 210.

The probe assembly 150 may also provide a means for measuring deformation 230 of the tube end 210 along the axial direction 182 (FIG. 6) and/or the circumferential direction 180 (FIG. 7). For example, by comparing distances that the ultrasonic sound waves travel at different axial locations of the tube end 210 and at different circumferential locations of the tube end 210, the integrity of the swaged joint of the fitting 218 to the tube may be ascertained. In this regard, Step 312 may further include determining the integrity of a swage joint 220 (FIG. 6) between the fitting 218 (FIG. 6) and the tube end 210 (FIG. 6) at a joint section 224 (FIG. 6) by comparing the diameter at the joint section 224 relative to the diameter at the non-joint section 226 (FIG. 6). The integrity of the swage joint 220 may be quantified by determining the difference 234 (FIG. 6) in diameter of the inner surface 214 at the joint section 224 relative to the diameter at a non-joint section 226.

Step 314 of the method 300 of FIG. 12 may include generating electrical signals 170 (FIG. 10) representative of the reflected sound waves 168 (FIG. 6). The electrical signals 170 may be transmitted to the computer 250 (FIG. 10) and/or the display device 254 (FIG. 10) for processing. Step 314 may include generating a graphical image 256 (FIG. 11) of the tube end 210' (FIG. 11) on the display device 254.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. A method of inspecting the integrity of a swage joint of a tubular workpiece, comprising:
    positioning a probe assembly adjacent to an inner surface of a tubular workpiece having a tube end, the probe assembly having a transducer array;
    generating transmitted sound waves propagating toward the tubular workpiece;
    receiving, at the probe assembly, reflected sound waves in response to impingement of the transmitted sound waves;
    rotating the probe assembly relative to the tubular workpiece such that the transducer array passes over the inner surface in a circumferential direction during generation of the transmitted sound waves; and
    measuring, during rotation of the probe assembly, a change in diameter of the inner surface of the tube end along an axial direction to verify the integrity of the swage joint.

2. The method of claim 1 wherein the step of generating transmitted sound waves comprises:
    generating the transmitted sound waves at a frequency of at least approximately 10 megahertz.

3. The method of claim 1 wherein the step of generating transmitted sound waves and receiving reflected sound waves comprises:
    generating the transmitted sound waves and receiving the reflected sound waves on a substantially continuous basis during rotation of the probe assembly relative to the tubular workpiece.

4. The method of claim 1 wherein the step of generating transmitted sound waves and receiving reflected sound waves comprises:
    generating, using the probe assembly, electrical signals representative of the reflected sound waves;
    receiving, at a display device, the electrical signals; and
    generating, on the display device, a graphical image representative of the inner surface during rotation of the probe assembly relative to the tubular workpiece.

5. The method of claim 1 further comprising the step of:
    maintaining the transducer array at a substantially constant distance from the inner surface during rotation of the probe assembly relative to the tubular workpiece.

6. The method of claim 1 further comprising the steps of:
    rotating at least one of the probe assembly and the tubular workpiece about a rotational axis; and
    radially adjusting a radial location of the probe assembly relative to the rotational axis such that the probe assembly is located at a predetermined distance from the inner surface.

7. The method of claim 1 further comprising the step of:
    clamping the tubular workpiece such that a tube end of the tubular workpiece is maintained in substantially centered relation to a rotational axis of the probe assembly during rotation thereof.

8. The method of claim 1 further comprising the step of:
    immersing in liquid the probe assembly and an area under inspection of the tubular workpiece; and coupling, using the liquid, the transmitted sound waves from the probe assembly to the inner surface.

* * * * *